US006863791B1

(12) United States Patent
Liu et al.

(10) Patent No.: US 6,863,791 B1
(45) Date of Patent: Mar. 8, 2005

(54) METHOD FOR IN-SITU CALIBRATION OF ELECTROPHORETIC ANALYSIS SYSTEMS

(75) Inventors: Changsheng Liu, State College, PA (US); Hequan Zhao, State College, PA (US)

(73) Assignee: SpectruMedix LLC, State College, PA (US)

( * ) Notice: Subject to any disclaimer, the term of this patent is extended or adjusted under 35 U.S.C. 154(b) by 620 days.

(21) Appl. No.: 09/676,526

(22) Filed: Oct. 2, 2000

Related U.S. Application Data

(60) Provisional application No. 60/231,574, filed on Sep. 11, 2000.

(51) Int. Cl.[7] ............................................. G01N 27/26
(52) U.S. Cl. ...................... 204/461; 204/452; 702/19; 702/20; 250/252.1
(58) Field of Search ............................... 204/452, 461; 356/344; 250/252.1, 341.5, 339.09; 382/128, 129; 702/19, 20, 85

(56) References Cited

U.S. PATENT DOCUMENTS

| | | | |
|---|---|---|---|
| 4,811,218 A | 3/1989 | Hunkapiller et al. ... | 364/413.01 |
| 5,871,628 A | 2/1999 | Dabiri et al. ................ | 204/461 |
| 5,993,634 A | 11/1999 | Simpson et al. ............ | 204/612 |
| 5,998,796 A | 12/1999 | Liu et al. .................. | 250/458.1 |
| 6,015,667 A * | 1/2000 | Sharaf .......................... | 435/6 |
| 6,017,434 A * | 1/2000 | Simpson et al. ............ | 204/612 |
| 6,027,627 A | 2/2000 | Li et al. ..................... | 204/603 |
| 6,333,501 B1 * | 12/2001 | Labrenz ................... | 250/341.5 |
| 6,821,402 B1 * | 11/2004 | Sharaf et al. ............... | 204/461 |
| 2002/0125136 A1 * | 9/2002 | Sharaf et al. ............... | 204/461 |
| 2002/0166767 A1 * | 11/2002 | McVey et al. .............. | 204/452 |

FOREIGN PATENT DOCUMENTS

| | | |
|---|---|---|
| WO | WO 97/46963 | 12/1997 |
| WO | WO 00/16087 | 3/2000 |

OTHER PUBLICATIONS

*International Search Report* dated Dec. 17, 2001 in PCT/US01/28281.

Zhongbin Yin et al., "Automated matrix–determination in four dye fluorescence–based sequencing", Electrophoresis, 1996, 17, pp. 1143–1150.

Welan Huang et al., "A method to determine the filter matrix in four–dye fluorescence–based DNA sequencing", 1997, 18, pp. 23–25.

* cited by examiner

*Primary Examiner*—Nam Nguyen
*Assistant Examiner*—Brian L Mutschler
(74) *Attorney, Agent, or Firm*—Fish & Richardson P.C.

(57) ABSTRACT

An electrophoretic system having a plurality of separation lanes is provided with an automatic calibration feature in which each lane is separately calibrated. For each lane, the calibration coefficients map a spectrum of received channel intensities onto values reflective of the relative likelihood of each of a plurality of dyes being present. Individual peaks, reflective of the influence of a single dye, are isolated from among the various sets of detected light intensity spectra, and these can be used to both detect the number of dye components present, and also to establish exemplary vectors for the calibration coefficients which may then be clustered and further processed to arrive at a calibration matrix for the system. The system of the present invention thus permits one to use different dye sets to tag DNA nucleotides in samples which migrate in separate lanes, and also allows for in-situ calibration with new, previously unused dye sets.

16 Claims, 18 Drawing Sheets

CLOSE-UP OF THE ELECTROPHEROGRAMS OF ONLY
FOUR SELECTED WAVELENGTH CHANNEL FOR SIMPLICITY.

REJECTED PEAK LABELLED WITH X BASED ON THE PEAK SPACING
CALCULATIONS AFTER THESE PEAKS IN A LOCAL SECTION HAVE BEEN PROCESSED.

| C | A | G | T |
|---|---|---|---|
| .408 | .037 | .021 | .016 |
| 1 | .205 | .034 | .021 |
| .887 | .722 | .063 | .023 |
| .566 | 1 | .244 | .027 |
| .394 | .721 | .754 | .067 |
| .265 | .428 | 1 | .359 |
| .152 | .287 | .691 | .925 |
| .091 | .202 | .403 | 1 |
| .059 | .120 | .274 | .604 |
| .040 | .069 | .202 | .316 |

BigDye TERMINATOR SET

*Fig. 13a*

| C | A | G | T |
|---|---|---|---|
| .448 | .079 | .026 | .021 |
| 1 | .379 | .058 | .027 |
| .944 | .847 | .223 | .035 |
| .685 | 1 | .670 | .067 |
| .451 | .806 | 1 | .274 |
| .287 | .557 | .844 | .765 |
| .173 | .373 | .528 | 1 |
| .108 | .249 | .357 | .784 |
| .116 | .162 | .248 | .480 |
| .050 | .099 | .163 | .300 |

RHODAMINE TERMINATOR DYE SET

*Fig. 13b*

| C | A | G | T |
|---|---|---|---|
| .877 | .333 | .291 | .379 |
| 1 | .789 | .358 | .439 |
| .840 | 1 | .515 | .404 |
| .617 | .771 | .849 | .386 |
| .418 | .488 | 1 | .541 |
| .279 | .312 | .802 | .862 |
| .205 | .218 | .557 | 1 |
| .151 | .150 | .399 | .834 |
| .102 | .095 | .284 | .563 |
| .068 | .061 | .191 | .365 |

ET PRIMER DYE SET

*Fig. 13c*

| C | A | G | T |
|---|---|---|---|
| .317 | .101 | .084 | .059 |
| 1 | .932 | .742 | .199 |
| .516 | 1 | 1 | .607 |
| .211 | .426 | .625 | 1 |
| .107 | .184 | .263 | .814 |
| .048 | .074 | .122 | .423 |
| .025 | .034 | .049 | .234 |
| .137 | .017 | .024 | .106 |
| .000 | .000 | .000 | .000 |
| .000 | .000 | .000 | .000 |

BODIPY PRIMER DYE SET

*Fig. 13d*

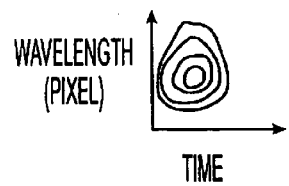
*Fig. 17a*
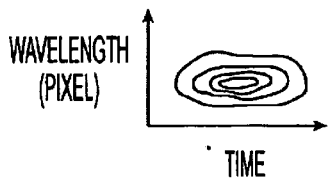
*Fig. 17b*
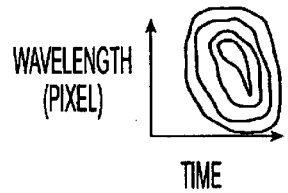 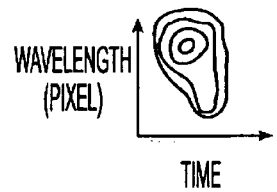
*Fig. 17c*  *Fig. 17d*
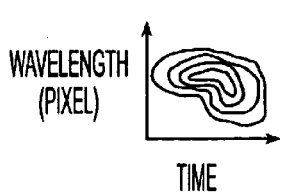 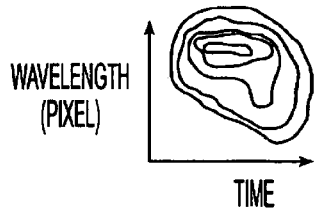 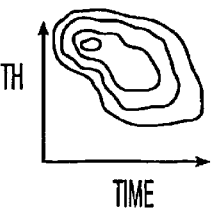
*Fig. 17e*  *Fig. 17f*  *Fig. 17g*

METHOD FOR IN-SITU CALIBRATION OF ELECTROPHORETIC ANALYSIS SYSTEMS

RELATED APPLICATIONS

This application claims priority to U.S. provisional application No. 60/231,574, filed Sep. 11, 2000.

TECHNICAL FIELD

The present invention is directed to electrophoresis equipment which identifies migrating species based on an analysis of detected fluorescence levels. More particularly, the present invention is directed to such equipment having an in-situ calibration capability so as to permit various dye sets to be used and a three dimensional graphical representation of results to allow for simplified base calling.

BACKGROUND

In the detector system in accordance with U.S. Pat. No. 6,027,627, fluoresced light from migrating species within a plurality of capillaries aligned in parallel passes through a filter, a transmission grating beam splitter and a lens before it impinges on a CCD detector array. In the preferred embodiment, the CCD detector array comprises 1024×256 pixels. The first dimension, (1024 pixels) covers 96 parallel capillaries, each capillary being focused onto at least one of the 1024 rows, although the number of rows per capillary can be increased by selecting a lens with a different focal length or changing other optical parameters. The second dimension (256 pixels) covers the fluorescence spectrum spread by the transmission grating.

In this prior art system, both the first order and second order components can be focused onto the detector array, although this is not an absolute requirement. What is required, however, is that a spectrum (such as represented by the $1^{st}$ order components) be created for each capillary and detected. The spectrum of interest should include the wavelengths of light at which the dyes are known to fluoresce. The spectrum of interest for each capillary is spread over P contiguous pixels and these are divided into R channels of Q contiguous pixels, R=P/Q. R should be at least as large as the number of dyes M being used and preferably is greater than this number.

The detector of the prior art system outputs a spectrum comprising R light intensity values for each capillary, each time that data is provided to the associated processor. The processor then maps the spectrum of R intensity values for each capillary, onto values which help determine which dye has been detected in that capillary. This is typically done by multiplying calibration coefficients by the vector of intensity values, for each capillary.

The principle behind the calibration coefficients is that a spectrum of received light intensities in each of the channels is caused by the spectrum of a single dye (tagging a corresponding base) weighted by the effects (calibration coefficients) of the detection system. If $I_0(n), I_1(n), \ldots, I_9(n)$ represent the measured intensities of the R=10 channels at the nth set of outputs from the CCD (after preprocessing including detection, binning and baseline subtraction), $B_0(n), B_1(n), \ldots, B_3(n)$ is a vector representing the contribution (presence 1 or absence 0) from of the M=4 bases, and $C_{ij}$ are coefficients of a known 10×4 matrix which maps the bases onto the detected channels, we then have the following relationship:

$$\begin{pmatrix} I_0(n) \\ I_1(n) \\ I_2(n) \\ \ldots \\ I_9(n) \end{pmatrix} = \begin{pmatrix} C_{00} & C_{01} & C_{02} & C_{03} \\ C_{10} & C_{11} & C_{12} & C_{13} \\ C_{20} & C_{21} & C_{22} & C_{23} \\ \ldots & \ldots & \ldots & \ldots \\ C_{90} & C_{91} & C_{92} & C_{93} \end{pmatrix} \begin{pmatrix} B_0(n) & B_1(n) & B_2(n) & B_3(n) \end{pmatrix}$$

Eq. 1 can thus be rewritten as:

$$I(n) = C\, B(n) \tag{Eq. 2}$$

Given a vector of intensities output by a CCD for each separation lane, the theory of determining the presence or absence of each of the M=4 bases from the R=10 wavelength channels is fairly well established. This is simply a particular case of an over-determined system in which a smaller number of unknowns is determined from a greater number of equations. After mathematical transformation, Eq. 2 can be written as:

$$B(n) = (C^T C)^{-1}\, C^T I(n) \tag{Eq. 3}$$

where $B_0(n), \ldots, B_3(n)$ now represent the unknown values of the individual bases as functions of time index n, each value being reflective of the relative likelihood of the corresponding dye tagging that base being present; $I_0(n), I_1(n), \ldots, I_9(n)$ are the fluorescence intensities of the ten channels, and $C_{ij}$'s are the coefficients of wavelength i under known base j and where $C^T$ is a transpose of the matrix C and $A=(C^T C)^{-1} C^T$ is the pseudo-inverse of matrix C. While in the above analysis, C is a 10×4 matrix because a total of ten channels and four bases are used, in the general case, C is an R×M matrix wherein R≥M, and R and M are both integers greater than 2.

Typically, in prior art systems, the calibration matrix C is determined at the time the system is created. More particularly, calibration matrix C is specific to a set of dyes that are used, and is constant for all separation lanes in a system. If such a prior art system is then modified, such as by upgrading to a new set of optical filters, the calibration matrix C needs to be re-calibrated.

FIG. 1 illustrates two shortcomings of using a constant calibration matrix for all capillaries in a capillary array. As seen in FIG. 1, the $0^{th}$ order spectral intensities 102 from each of the capillaries do not map onto the same pixel in corresponding pixel columns. In particular, the $0^{th}$ order spectral intensities from capillaries 7 and 10, which are detected in their corresponding pixel columns 104, 106, respectively, do not fall on the same-positioned pixel as do the $0^{th}$ order spectral images from the remaining capillaries. Similarly, the $1^{st}$ order spectral intensities 112 from capillaries 7 and 10 in these same columns also do not fall on the same-positioned pixels as do the $1^{st}$ order spectral images from the remaining capillaries, but rather are offset by a skew of a single pixel. A consequence of this skewness, which may be caused by improper arrangement of capillaries 7 and 10 within the capillary array, is that the binning process for $1^{st}$ order intensities from capillaries 7 and 10 results in a spectrum which would be slightly different than if the binning process started one pixel over. As a result, using a single calibration matrix C for all the capillaries, leads to imprecise results, when Eq. 3 is invoked to try to identify the due causes the detected fluoroscence from capillaries 7 and 10. As also illustrated in FIG. 1, the $1^{st}$ order spectral image 114 for capillary 1 maps onto one more pixel than do the spectral images of the remaining capillaries. This feature, which may be caused by such factors as coma, spherical aberrations, astigma, and lateral chromatic aberration of the grating image system, also may lead to imprecisions when binning followed by use of the calibration matrix as in Eq. 3.

In general, different dye sets have different spectra. As a consequence, each dye set has a different calibration matrix. Consequently, a further disadvantage of using a single calibration matrix for a multi-lane separation system, is that one cannot run multiple dye sets in different separation lanes.

SUMMARY OF THE INVENTION

In one aspect, the present invention is realized by a multi-lane electrophoretic separation apparatus which simultaneously utilizes multiple calibration matrices which calibrate for different dyes used to tagged migrating species.

In another aspect, the present invention is realized by a multi-lane electrophoretic separation apparatus in which a calibration matrix is calculated in-situ.

In yet another aspect, the present invention is realized by a multi-lane electrophoretic separation apparatus in which a calibration matrix is calculated for each lane.

In yet another aspect, the present invention is realized by a method for calculating a calibration matrix from data acquired from a sample. The method includes the steps of detecting emitted fluorescence spectra from a plurality of tagged migrating species, clustering the detected peaks into a number of groups, and then calculating calibration coefficients representative of at least some of the groups. After detection, and prior to grouping, the peaks may be culled to ensure that only peaks having a high probability of being associated with a particular group, are used to calculate the calibration coefficients.

BRIEF DESCRIPTION OF THE DRAWINGS

The present invention is better understood and illustrated through the drawings in which:

FIG. 9b shows a histogram for the clustered peaks corresponding to three dyes of FIG. 9a;

FIGS. 13a–13d present calibration coefficient matrices for each of four dye sets commonly used in DNA sequencing.

FIGS. 17a–17g shows typical morphologies seen in contoured time-frequency plots, such as those shown in FIGS. 14–16.

DETAILED DESCRIPTION OF THE PREFERRED EMBODIMENT

The preferred system on which the present invention can be used is an automated capillary electrophoresis system, such as is described in U.S. Pat. No. 6,027,627. The preferred detector arrangement for such a system is shown in U.S. Pat. No. 5,998,796. The contents of both of these are incorporated by reference to the extent necessary to understand the present invention.

The present invention is described with reference to a detector system in which a total of P=30 pixels are binned into R=10 wavelength channels of Q=3 pixels each. The binning is done onboard the CCD array chip under software control. For DNA sequencing, the number of dyes M is 4—one for each nucleotide—and the spectrum of interest is in the range of 520 nm to 670 nm. Thus, the spectral resolution of the 10 wavelength channels is about 15 nm each. During data collection, for each of the 96 capillaries, 10 data points are offloaded each time the CCD array is read out and these values are stored for subsequent analysis. Furthermore, during an electrophoresis run, data from the CCD array is offloaded periodically, at a sample rate of f samples per second. Thus, during a run which lasts time T, a total of N=fT samples are taken.

Figure 2:
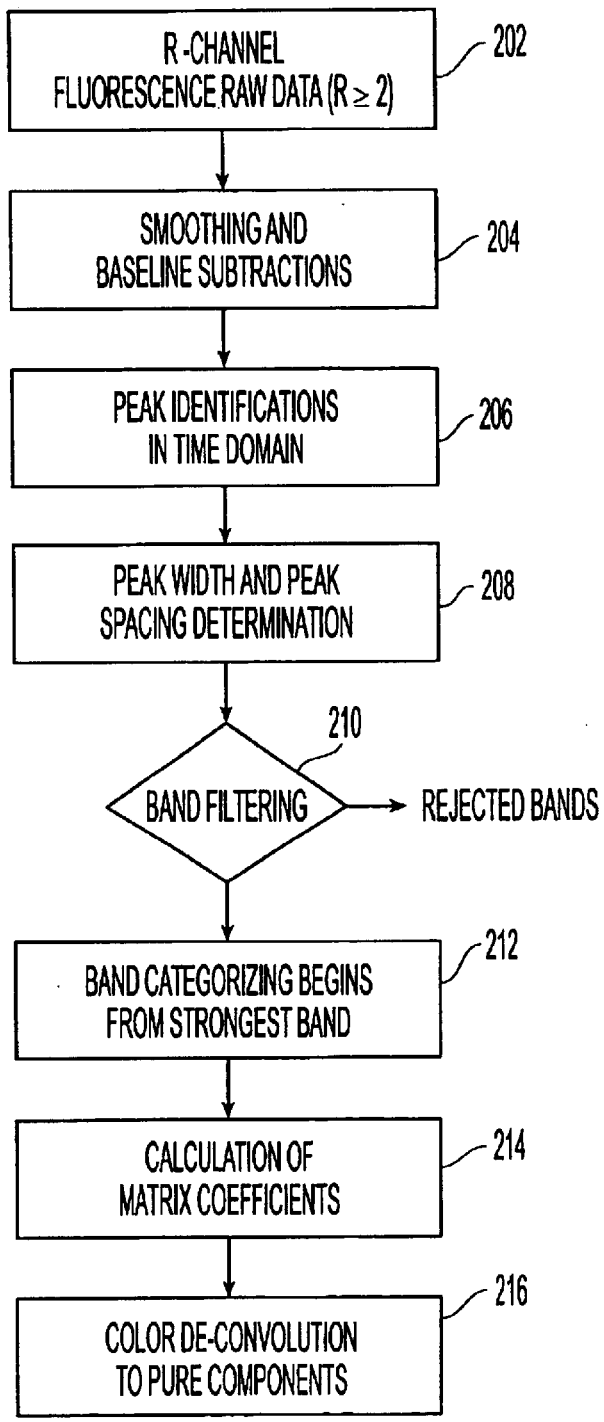
FIG. 2 shows a flow chart outlining the steps in calculating a coefficient matrix in accordance with the present invention.
Figure 3:
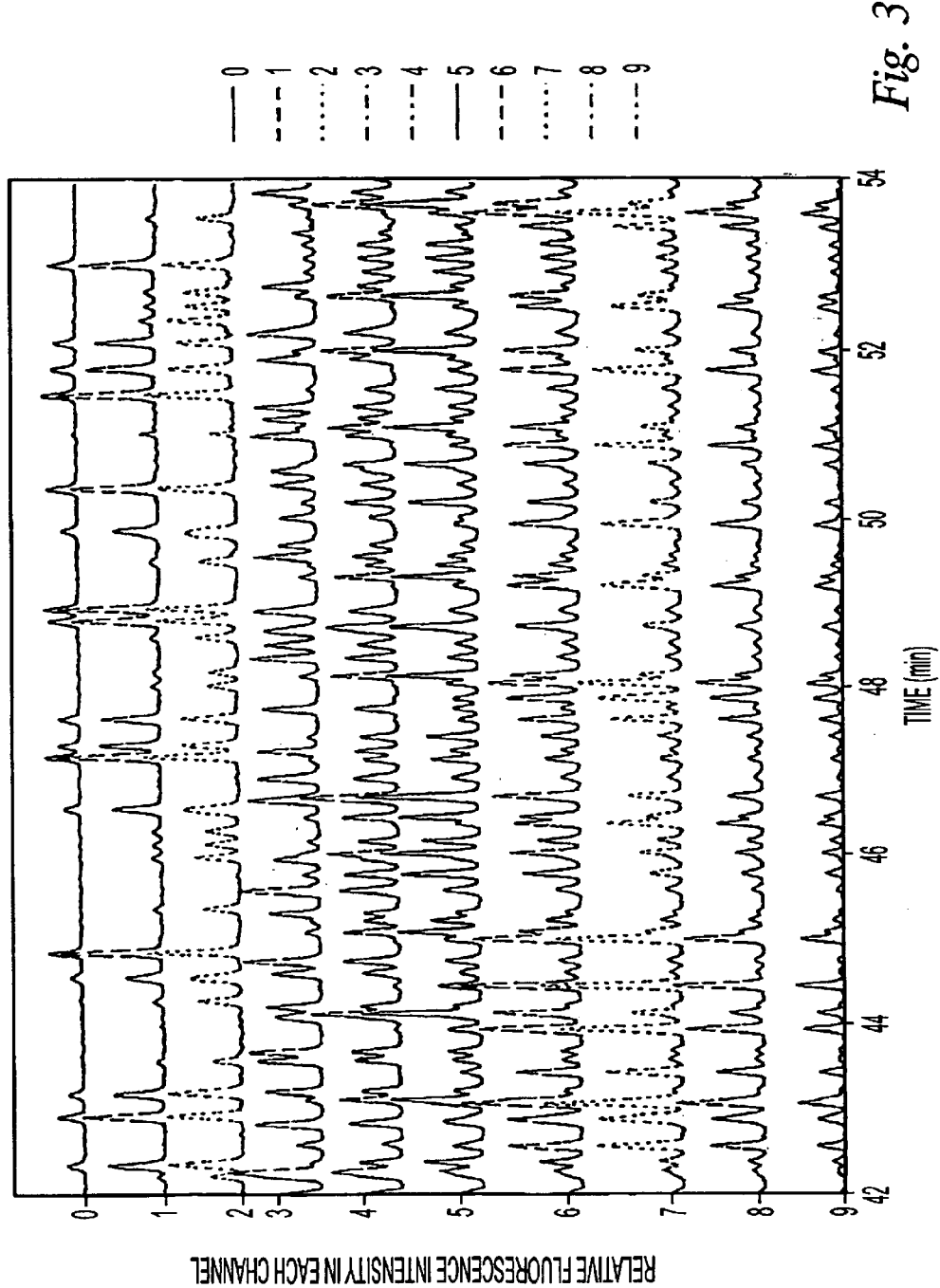
FIG. 3 presents the exemplary detected intensity over 10 channels derived from the detector array.

FIG. 2 presents a flowchart 200 depicting the general steps in calculating a coefficient matrix for each capillary in accordance with a preferred embodiment of the present invention. In step 202, R-channel fluorescence data from a single capillary is collected for a predetermined period of time. FIG. 3 presents a graphical illustration of light intensity time series data for a total of R=10 channels. In step 204, smoothing and baseline subtraction is performed on the original data to eliminate trends. In step 206, peaks are identified in the time domain. In step 208, peak widths and peak spacing metrics are calculated. In step 210, the metrics are used in conjunction with the identified peaks to eliminate peaks from consideration for forming the coefficient matrices. In step 212, the remaining peaks are ranked so that the strongest peaks are used. In step 214, the coefficients of the calibration matrix are calculated. Finally, in step 216, the calibration matrix is used to perform spectral deconvolution to identify migrating samples. These steps are now described in further detail.

Step 204—Data Smoothing and Baseline Subtractions. The raw data are smoothed by Savitzky-Golay method for a few close points, e.g., 1, 3, 5, 7, 9 points, as determined by a user of the present invention. In general, the data would not be smoothed if 1 point is chosen. The base lines of the smoothed data in the ten channels are subtracted with software that runs on the processor associated with the detector system. The software searches local minimum of every local section, for example, 300 data points in a channel as a section. A straight line, baseline, connects the two minimums in the consecutive sections. The values of raw data between the two local minimums are subtracted to the baseline value. The new values after the baseline subtraction and smoothing are stored for further process. The order of data smoothing and baseline subtraction can be reversed.

Step 206—Peak-picking in time domain. The properties of each wavelength channel after baseline subtraction are calculated before peak-picking. These properties include global average signal intensity, global average intensity deviation between two consecutive points, local maximum and local average deviation in a predetermined number of sections, preferably 40.

global average intensity:

$$I_{g,ave} = \frac{\sum_{j=m}^{0} I_j}{m} \quad \text{(Eq. 4)}$$

global average deviation:

$$I_{g,dev} = \frac{\sum_{j=m-1}^{0} |I_{j+1} - I_j|}{m-1} \quad \text{(Eq. 5)}$$

local maximum: $I_{l,max} = \max(I_k, I_{k+1}, I_{k+2}, \ldots, I_{k+3})$ (Eq. 6)

local average deviation:

$$I_{l,dev} = \frac{\sum_{j=s-1}^{0} |I_{k+j+1} - I_{k+j}|}{s-1} \quad \text{(Eq. 7)}$$

where $I_j$ represents the intensity at point j, m is the total number of data points, s is the number of data points in a local section, and k is the starting point in the section.

The above four parameters for each of the ten channels, at appropriate points along the sampled intensity values are used in a heuristic algorithm for determining peaks. A point $I_j$ in a given channel is considered to be a peak if it meets the following criteria:

(1) $I_j$ is a local maximum among five consecutive points: $I_j > I_{j-1} > I_{j-2}$ and $I_j > I_{j+1} > I_{j+2}$;

(2) Ij is greater than 20% of the section maximum and is also greater than 40% of global average intensity: $I_j > 0.2\ I_{s,max}$; $I_j > 0.4\ I_{g,ave}$;

(3) At least one of the two edge deviations on either side of $I_j$ must be greater than 70% of the section average deviation and greater than 20% of global average deviation: i.e., e.g.

right edge deviation: $(I_{j+1} - I_{j+3})/2 > 0.7\ I_{l,dev}$ and $(I_{j+1} - I_{j+3})/2 > 0.2\ I_{g,dev}$, or left edge deviation: $(I_{j-1} - I_{j-3})/2 > 0.7\ I_{l,dev}$ and $(I_{j-1} - I_{j-3})/2 > 0.2\ I_{g,dev}$, or both;

(4) Peak assembly. This is a process to remove a peak that occurs only in one channel (i.e., a peak that is not physically sound) and to determine whether the peak maximum has been shifted one frame due to mathematical manipulation, and then determine the proper band location in the time domain. Sometimes peak maxima may shift a frame in the time domain. It is the same peak even if the peak position is shifted a frame in different color channels. Peak intensities in all of the channels are summed in the time domain.

FIG. 3 depicts a portion of the raw time series intensity data Xj, j representing the time index of the sample, for each of the 10 channels from a single capillary during a DNA sequencing run. At any given instant, only a few channels exhibit a peak because each of the four dyes only has a finite bandwidth. The raw data intensity signals Xj from each of the 10 channels, for each capillary, are stored for future processing to create the multicomponent matrix and also to identify the fluorescent species giving rise to the detected fluorescent intensities. The peak-picking process is carried out through all of the 10 traces to give the peak position in time domain. A peak due to the specific type of molecules in the sample will show up at a specific time in more than a trace because of the spectra overlapping. For example in FIG. 3, a peak at 52 min has shown up in trace 3 to trace 9. The peak-picking program will pick up the peak from trace 3 to trace 9. At peak at 51.9, just prior to the peak at 5000, has shown up from the trace 0 to trace 6. At the specific time that a peak shows up in more than one channel, the peak intensities for all 10 channels are recorded for the data processing step. The channel number of maximum intensity over all of the ten channels is also recorded at the specific time.

Step 208—Peak spacing determination.

Figure 4A:
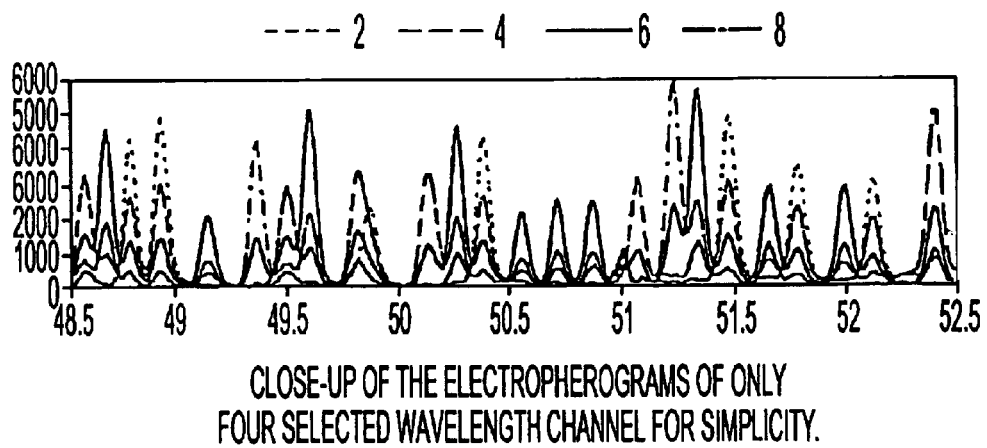
FIGS. 4a and 4b show intermediate results from peak spacing determination.
Figure 4B:
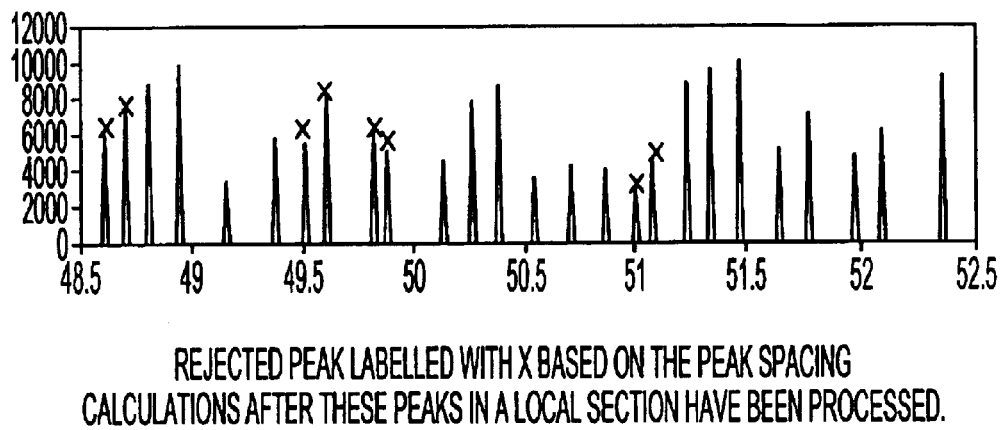

(a) Peak spacing in a local section. In the local section, peak spacing can be considered as a constant. After all of the peaks are determined from the last step shown in FIG. 4b. Average peak spacing $\Delta t_{sp,ave}$, in the local section is calculated based on the all of the identified peaks shown in FIGS. 4a and 4b. The average peak spacing is 12.5 frames. A pair of peaks is retained for the coefficient calculation if the spacing of the consecutive spacing is bigger than 75% of the average peak spacing or: $\Delta t_{sp} > 0.75\ \Delta t_{sp,ave}$. Thus, the peaks marked with X in FIG. 4b are rejected from the coefficient calculation.

(b) Identifying the overlapped peaks by peak-fitting software. After these peaks are identified, peak widths can be identified with a peak-fitting software. In most electrophoresis separations, the peaks coming out at the first section of the electropherogram are usually very sharp and the peaks in the late section of separation usually wide. However, the peak widths in a small local section, for example, in 300 frames, are practically the same. This concept is very important to resolve the temporal overlapping peaks in a local section. In DNA analysis, the complete overlapping bands with different DNA size in time domain are rare. Most of the overlap is confined to the rising or tailing edge of the peaks where one enters into the detection window and the other is moving out the windows. The overlapping peaks often are 30% wider than single peak in DNA separation. If intensity of a peak in a channel is small, 20% of local maximum intensity, we did not calculate the peak width due to its low intensity. The peak width and spacing at a specific moment can calculate from the ten traces of the data.

Figure 5:
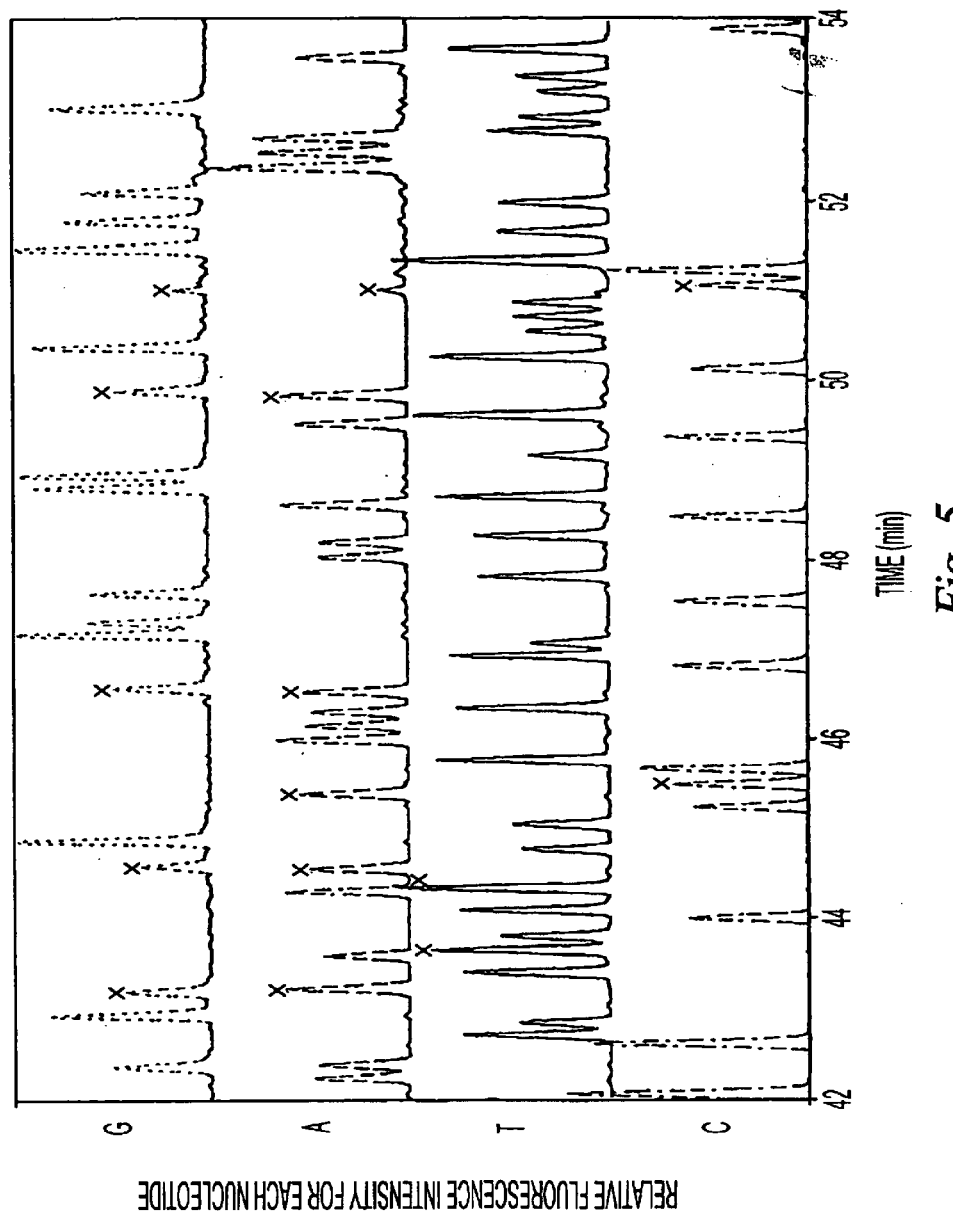
FIG. 5 shows relative fluorescence of the candidate peak intensities for each nucleotide.

Step 210. Peak Filtering & Spike Rejection. The width of a normal peak is usually between 4 to 20 frames. In contrast, spikes usually happen in one frame and appear as very sharp peaks. The spikes can result from cosmic ray pickups by the camera, thermal noise due to overheating of the camera, and sample impurity. Spacing criteria. If the peak spacing is 75% greater than the average speak spacing, the two peaks are retained for the coefficient calculation. Another way is to use both the peak width and spacing. If the average of two widths of adjunct peaks at their half intensity is bigger than peak spacing, the two peaks are rejected from the calculation of the matrix coefficients. There are two cases for the overlapped peaks. In one case, the two peaks are from the same dye tagging to the DNA molecules. There are not separated because of poor separation resolution. We find that this case would not cause any problem in matrix calculation since they are from the same dye. However, we would prefer to reject this type of peaks in the matrix calculation as a general rule of peak width. The other kind of case is that the two peaks are from different dyes tagging the DNA molecules with size difference of 1 base pair. We found that these two dyes are usually somewhat separated in time domain, but not completely resolved. Therefore the peak positions in all of the channels are differed by a few (2–3) frame number. Peak fitting will attribute them as overlapping peak. Rejecting these bands is important for the matrix calculation. Intensity criteria. If a peak whose maximum intensity is only 20% of the average peak intensity in a local section, the peak is rejected for the calculation of matrix coefficients. The small peak will cause significant errors for the matrix coefficients. FIG. 5 shows the relative fluorescence candidate peak intensity plots, one for each of the four nucleotides. The peaks labeled with * are rejected due to the spacing criteria. Most of these rejected peaks happen in the occasion of G after A. The mobility shift causes the two peaks to overlap.

Step 212. Based Categorization (Clustering)

If a band has passed the above-described filtering process, the band will go to the band categorizing (clustering) process. The band intensity is determined from a data channel that is sum of the intensity over all of the wavelength channels. This channel signal, in most cases, is from $0^{th}$-order of the grating, which has not any color-dispersed power. Another more preferable ways is to create this channel of the data that is the sum of the intensities over all of the channels.

Figure 6:
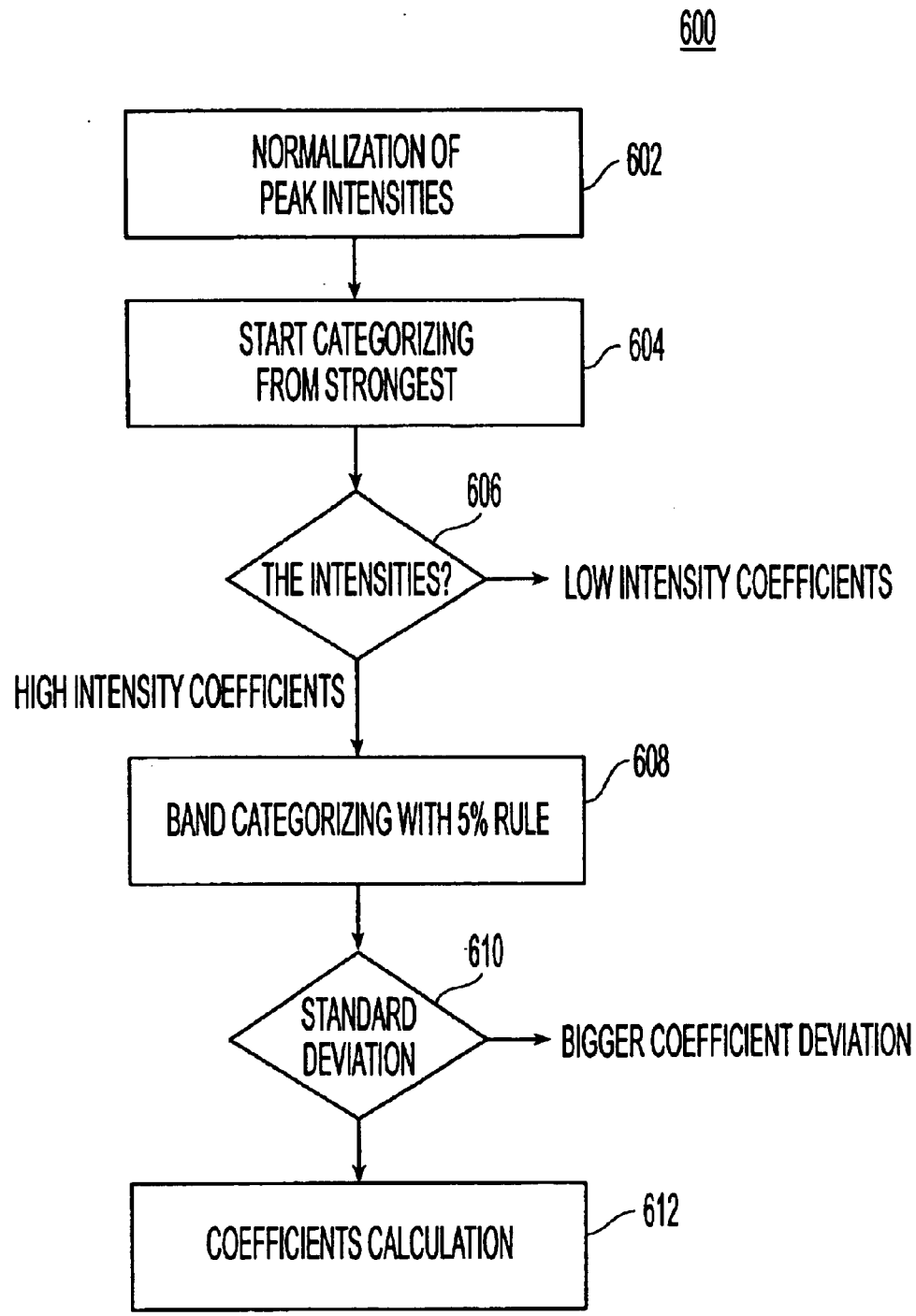
FIG. 6 depicts the process for characterizing peaks which remain after initial culling.

FIG. 6 shows a flowchart 600 representing the characterization of the remaining peaks, which thus correspond to the remaining detected bands. In step 602, the remaining peak intensities are normalized. In step 604, the band categorization commences with the strongest band. In step 606, the normalized intensities within a spectral set are compared and only those which have a significant value above the noise level are retained. In step 608, the bands are clustered if the differences in corresponding normalized coefficients are less than 5% of maximum intensity (0.05 where the maximum has been normalized to 1.0). In step 610, the average and standard deviation of the coefficients from a set of bands which have been clustered are calculated. Finally, in step 612, the coefficients for the calibration matrix are calculated. The steps described above are best illustrated using examples.

Step 602—Normalizing intensities. The following example is a set of data extracted from FIG. 5 at a time of 53.89 min corresponding to base C. Table 1 shows the intensity values for this set of data, which is normalized to 1.0.

the strongest band, then goes to next of the strongest, and so on. If a band shows up in a few channels at a specific time as peaks, then the intensity is normalized over all of the intensities in other channels as a matrix coefficient. There are certain advantages to choosing the band with the strongest intensity first and then second strongest and so forth. Because of instrument noise, the coefficient calculation of the strongest bands is more accurate than the low intensity bands. Accordingly, the effects of the leading and trailing portions of spurious peaks have lesser overall effect on a stronger band, than on a weaker band.

Step 606—Intensity culling; noise effects; low intensity and coefficients. In a preferred implementation, the overall noise level from all noise sources, such as shot noise, CCD reading noise, and CCD dark noise, is on the order of about 50 counts. Mathematical manipulation of the raw data, such as baseline subtraction and smoothing, can also introduce noise to the data. In a preferred embodiment, the data intensity is chosen to be about three times (150 counts) the noise level, and so this value is selected as a threshold. This criteria is consonant with conventional statistical principles. Thus, if the data intensity is lower than 150 counts, it preferably is not used for band categorizing. For example, in Table 1, the data in channels 0, 1, 2 and 3 are less than 150 and so their coefficients 0.0114, 0.021, 0.0198, and 0.0158 are not be used for categorizing. These coefficients are called un-comparable coefficients which are likely to cause calculation errors, and so are discarded.

Step 608—Band categorizing. If the difference in the comparable coefficients of two bands is less than 5% of maximum intensity (or 0.05 unit), the two band are clustered as being in the same category. Table 2 shows an example with 7 sets of coefficients, each set having been individually normalized. In the bands shown in Table 2, bands 1, 3, 4 are in the same category, because none of their coefficients differ by more than 0.05. However, band 1 and band 2 have coefficient differences of more than 0.05 unit and so are considered to be in different categories. Using the 5% rule,

TABLE 1 raw data, coefficient calculation, and un-comparable data.

| Channel | 0 | 1 | 2 | 3 | 4 | 5 | 6 | 7 | 8 | 9 |
|---|---|---|---|---|---|---|---|---|---|---|
| Intensities | 31 | 58 | 54 | 43 | 160 | 962 | 2538 | 2729 | 1691 | 840 |
| Norm. Coeff | 0.011 | 0.021 | 0.019 | 0.015 | 0.058 | 0.352 | 0.930 | 1 | 0.619 | 0.307 |

Step 604—Band Clustering Starting with the Stronger Bands. The process of band pattern recognition starts from it is evident that bands 5 and 6 are in the same category and band 7 forms its own category.

TABLE 2

Peak Clustering

| | | | | | | | | | | |
|---|---|---|---|---|---|---|---|---|---|---|
| Band 1 | 0.015 | 0.016 | 0.014 | 0.011 | 0.043 | 0.305 | 0.858 | 1 | 0.635 | 0.331 |
| Band 2 | 0.021 | 0.024 | 0.039 | 0.218 | 0.718 | 1 | 0.700 | 0.425 | 0.289 | 0.211 |
| Band 3 | 0.012 | 0.012 | 0.018 | 0.017 | 0.055 | 0.322 | 0.879 | 1 | 0.628 | 0.321 |
| Band 4 | 0.004 | 0.020 | 0.017 | 0.016 | 0.054 | 0.306 | 0.861 | 1 | 0.627 | 0.334 |
| Band 5 | 0.347 | 1 | | 0.948 | 0.612 | 0.423 | 0.288 | 0.162 | 0.096 | 0.063 | 0.049 |
| Band 6 | 0.336 | 1 | | 0.952 | 0.612 | 0.427 | 0.290 | 0.183 | 0.105 | 0.066 | 0.047 |
| Band 7 | 0.024 | 0.163 | 0.665 | 1 | 0.756 | 0.436 | 0.292 | 0.199 | 0.118 | 0.075 |

Upon considering the data in table 2, one may think it adequate to always categorize bands based on the maximum normalized peak. This, however, is not always the best approach. In some cases, the channel having the maximum intensity can be in either of two close channels for the same type of bands. For example, if two bands have their coefficients of 0.9948, 1 and 1, 0.982 in, say, channels 2 and 3, respectively, one might consider the two bands to belong to different categories, if only a maximum intensity rule is used. However, a system using the 5% of the maximum intensity rule will always take these two peaks as the same type of bands.

Figure 7A:
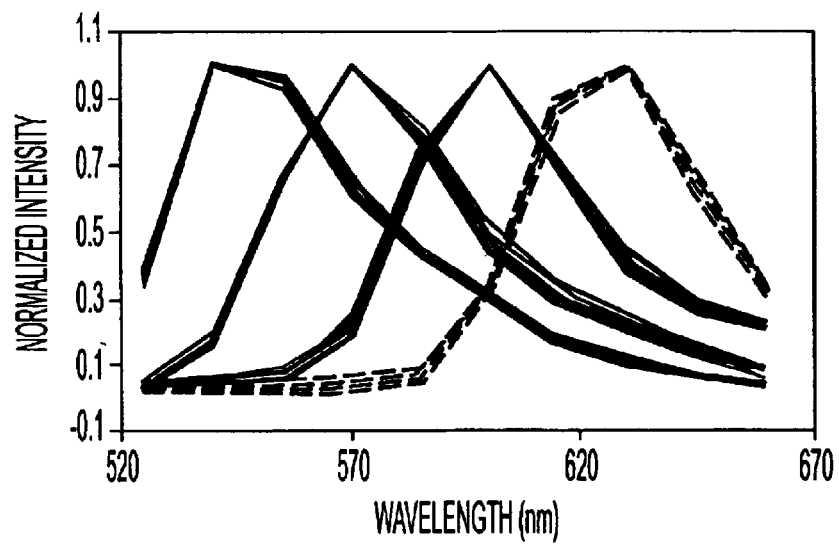
FIG. 7a represents plots for each cluster of nucleotides.
Figure 7B:
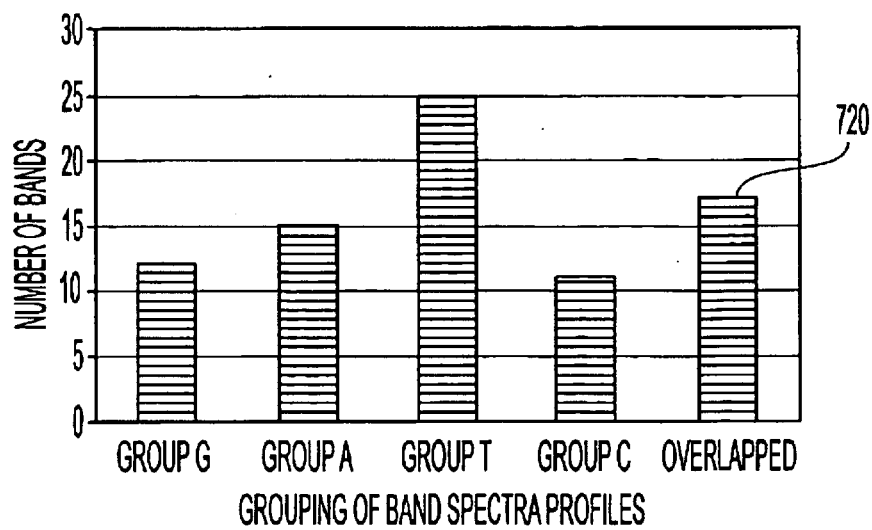
FIG. 7b represents histograms for the isolated peaks.

On occasion, a computer may automatically cluster the bands into more dye spectra than the number of dyes used in the electrophoresis. This results in a fake cluster 720, as seen in FIG. 7b. The fake cluster is results in a fake dye spectrum caused by overlapping peaks. The number of such overlapping peaks, following the various processing and culling, is preferably small, as compared to the number of real DNA spectra. In the event such a fake spectrum (and the corresponding extra cluster) arises, one may increase the 5% rule to 7% to see whether the overlapped bands merges into one or more of the other clusters bands. The coefficients of these fake bands can be represented as a combination of the spectra of the high occurrence bands. If the low occurrence bands can be written as a combination of the two high occurrence bands with two positive distribution, this type of low occurrence bands are fake band. After recognizing a fake bands with two of the above properties, these fake spectra are rejected from the coefficient calculation.

Step 610—Standard deviation rejection. The average and the standard deviation of each set of coefficients are calculated after the band categorizing process. If the deviations of the normalized coefficients for a given of set are greater than 130% of the standard deviation, the corresponding band should be rejected for the coefficient calculation.

Step 612—Coefficient calculation. After clustering, the coefficients of the sets within each of four clusters (one cluster for each nucleotide) can be plotted, as seen in FIG. 7a to verify that the clustering was properly performed and the desired number of clusters has resulted. The average of the coefficients of each of the sets is then taken to form an R-length vector (®=10 in a preferred embodiment), and each such R-length vector corresponds to one of the four columns in the coefficient matrix C.

Step 216 Color (Spectral) Deconvolution. During use, the pseudo-inverse of coefficient matrix C calculated for each separation lane is used to map a detected set of intensities from that separation lane, onto a decision vector B, as given in Eq. 3. The position of the highest value in the decision vector B corresponds to the identity of the dye.

The use of the techniques described above are now illustrated using examples.

Example A. DNA Sequencing Analysis

Experimental condition: capillary ID 75 um, OD 200 um, total length 80 cm, effective length (from injection end to detection window) 55 cm. Separation voltage 150 v/cm (12 kV). 96 capillaries are arranged parallel on a plane to form a capillary array.

Injection: 6 kV for 1 min. DNA sequencing sample: labeled PE Biosystem BigDye.

Excitation: all-line Ar ion laser emitting between at 450–520 nm (514.5 nm and 488 nm are two strongest emission lines). Laser light is spread over a 96-capillary array by cylindrical lenses. Detection: Nikon camera lens with focal length 85 mm and F1.4 is used to collected the fluorescence from the capillary array. The fluorescence then pass through longpass optical filter (cutoff 525 nm) (Optical Omaga Inc., CT) and a transmission grating (Edmund Scientific, NY) and impinge on a CCD camera (PixelVision, WA). The resolution of the system is about 5 nm/pixel. Every three consecutive pixels is binned and each channel represents the fluorescence intensity over 15 nm.

Figure 1:
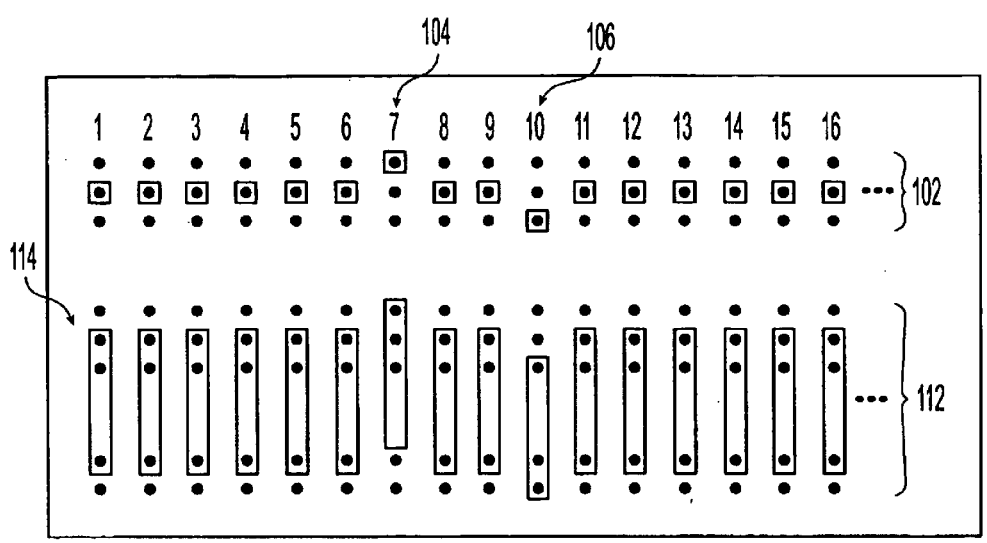
FIG. 1 shows imaging of zero- and first-order components onto a detector array.

Gel and separation conditions. The gel is a 5% linear polymer gel with 7 M. The DNA in FIG. 1 were separated at room temperature.

FIG. 3 shows the electropherograms of 10 wavelength channels for DNA sequencing in a time window from 42 min to 54 min. Top trace shows the blue channel at 525 nm. The next one trace is the data at 540 nm and so on. The bottom channel shows the red channel at 650 nm. The traces are constantly shifted for a better view.

FIG. 7a shows the spectra profiles of several resulting DNA bands. The bands are classified into four categories, each of which correspond to one of the four bases. FIG. 7b shows the number of bands in each category, and the group 720 of overlapped bands are rejected from the coefficient calculation. Most of the overlapped bands take place at the case of G immediately after A. Since the DNA fragments ends with G moves a little faster than that of A, the two peaks overlap during the instance of G immediately after A.

FIG. 5 shows the four traces that have automatically been deconvoluted. The four traces are fragments of G, A, T, C from the top to the bottom. The bands labeled with * are the bands that have been rejected.

Example B—DNA Fragment Analysis

Figure 8:
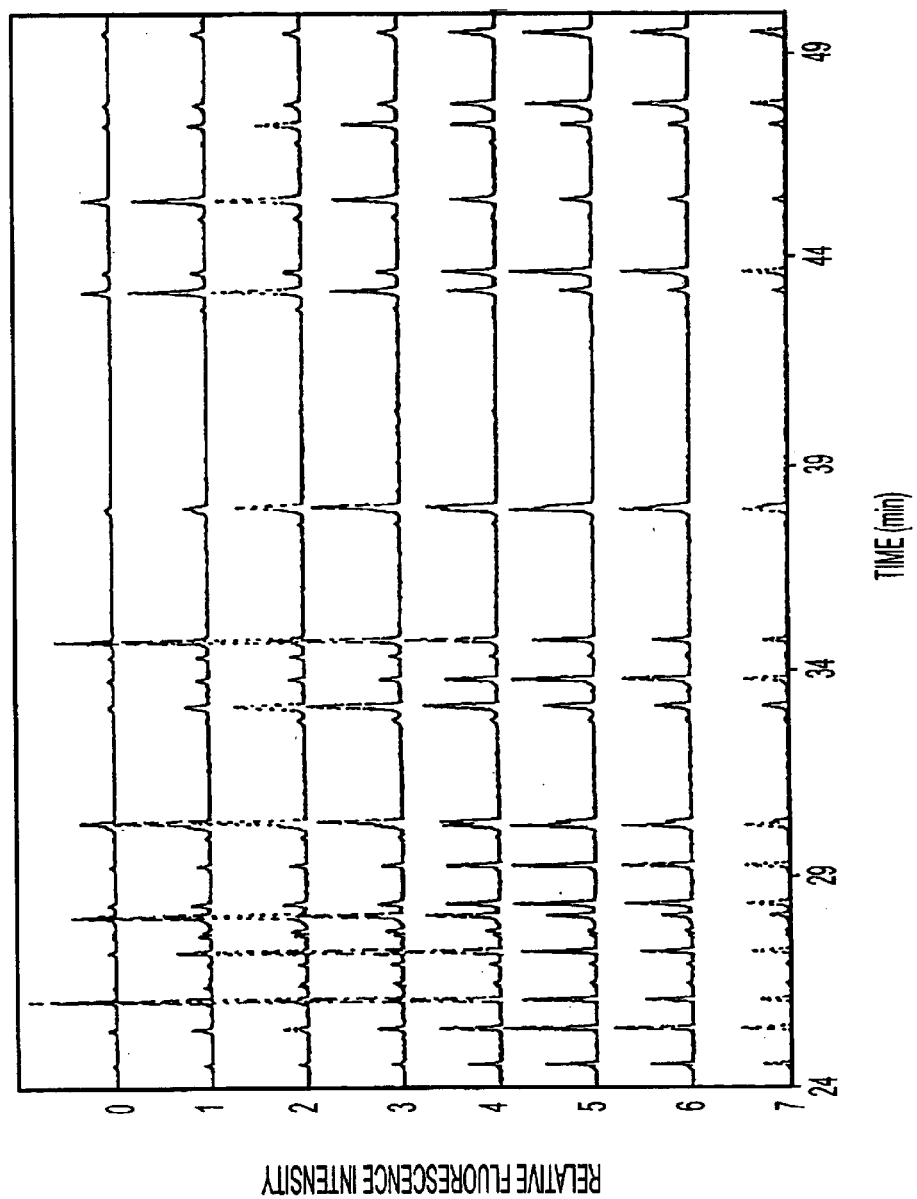
FIG. 8 shows thinned peaks for seven channels of data for an example in which three dyes are to be calibrated.
Figure 9A:
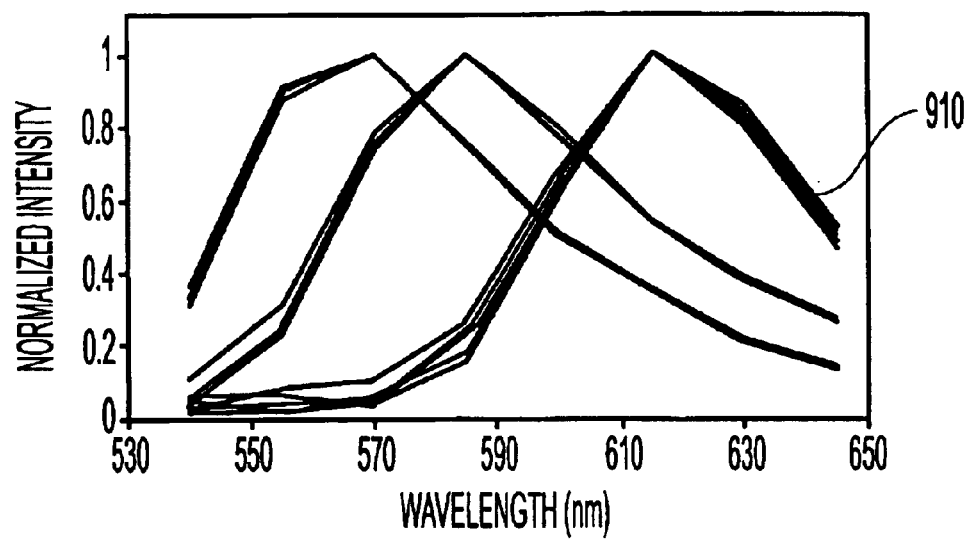
FIG. 9a shows coefficient plots for the three dyes used in conjunction with FIG. 8.
Figure 9B:
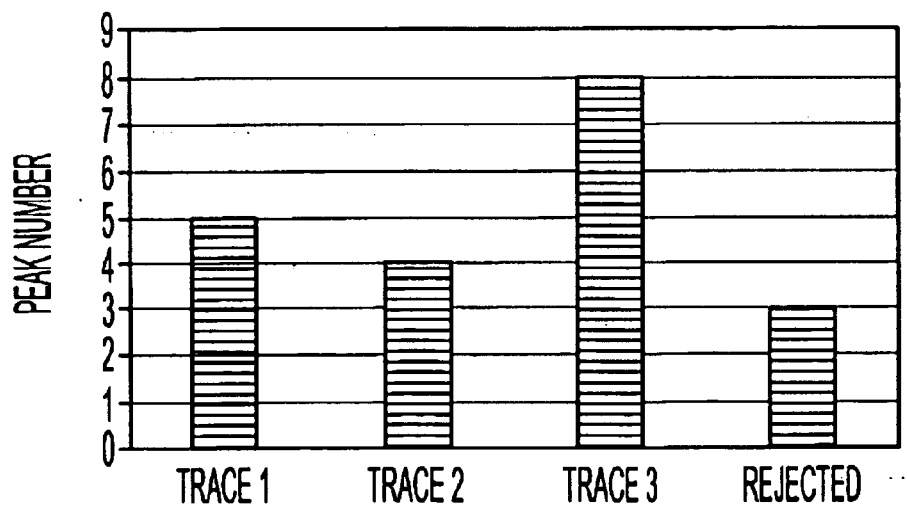
Figure 10:
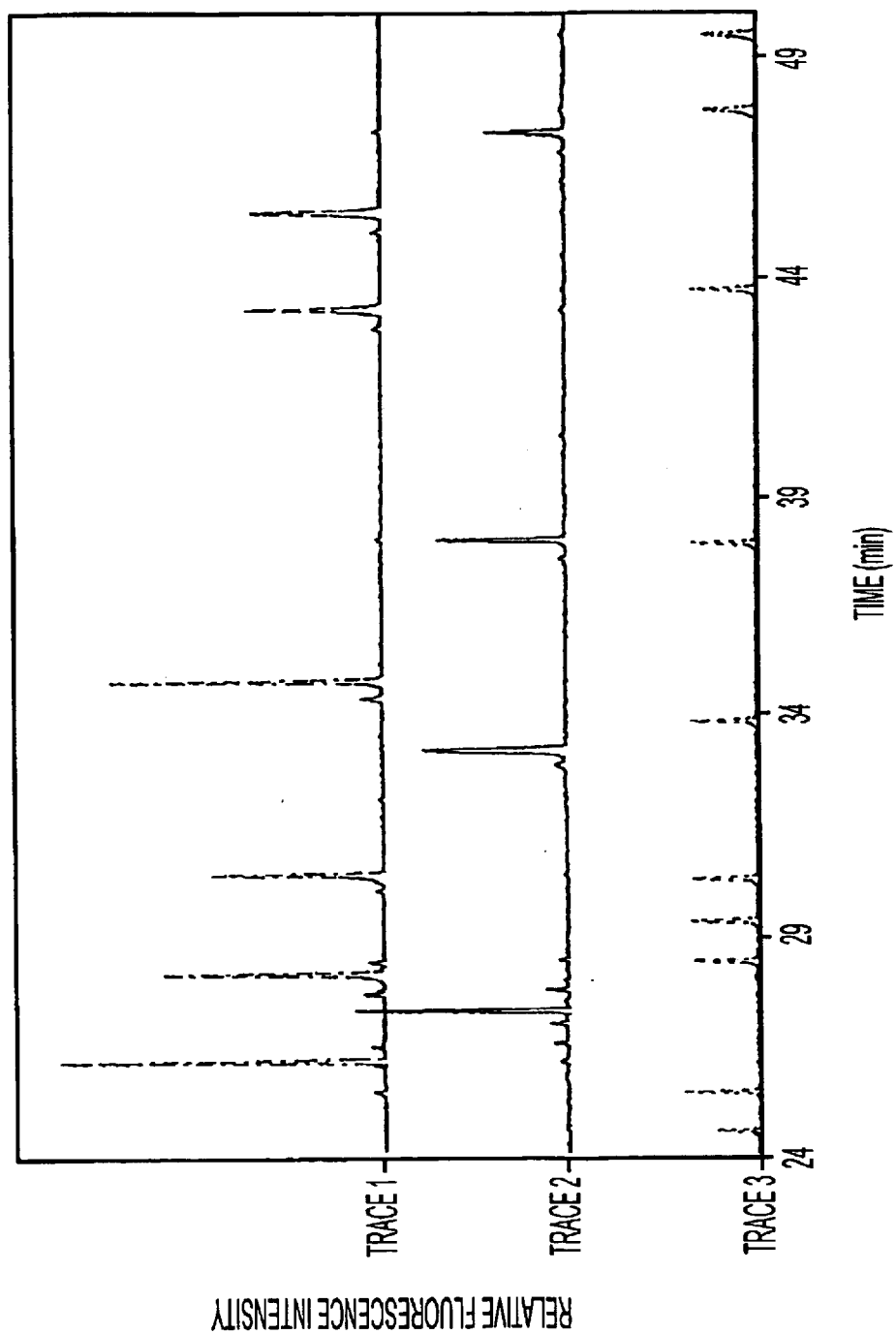
FIG. 10 represents the deconvoluted data for each of the candidate dyes of FIGS. 8–9b.

FIGS. 8, 9 and 10 show the data of DNA fragments. The gel in this experiment is 5% polymer gel without any urea. The temperature of separation was regulated at 80° C. The three types of dyes are used to label DNA fragments. The eight traces of the data are shown in FIG. 8, which is similar to DNA sequencing. The bands are automatically classified into three types of spectra. Then the coefficients of the three types of bands are automatically calculated to deconvolute into three distinct traces shown in FIG. 10. Trace 3 is a standard sample GeneScan 500 from PE Biosystem (CA). This section shows the DNA size from 60 to 350 basepairs, specifically 75, 100, 139, 150, 160, 200, 250, 300, 340, 350 basepairs. Since the intensity of this trace is lower the other traces, the corresponding spectra profile 910 in FIG. 9a shows more variation.

Example C—CZE (Capillary Zone Electrophoresis) For Protein Separation

Figure 11A:
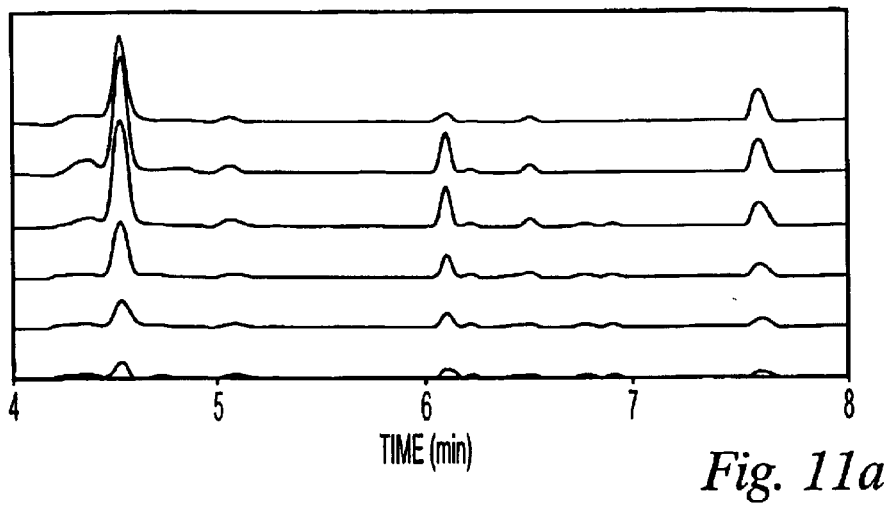
FIGS. 11a–11c present experimental results for identifying proteins.
Figure 11B:
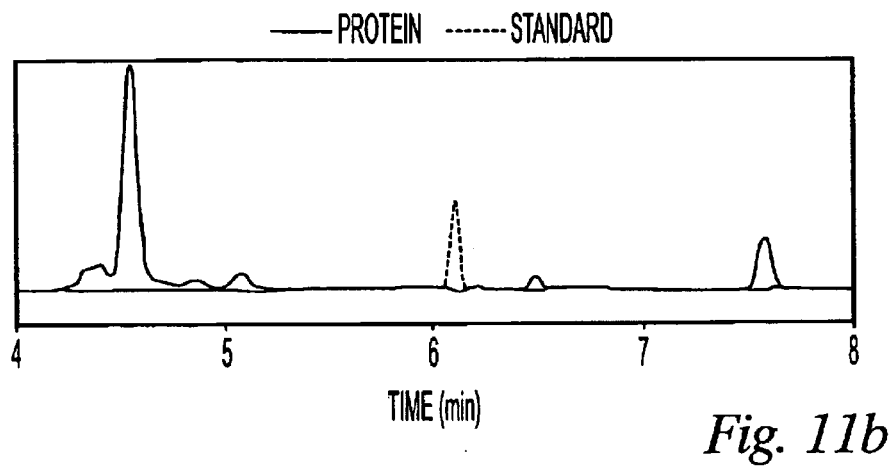
Figure 11C:
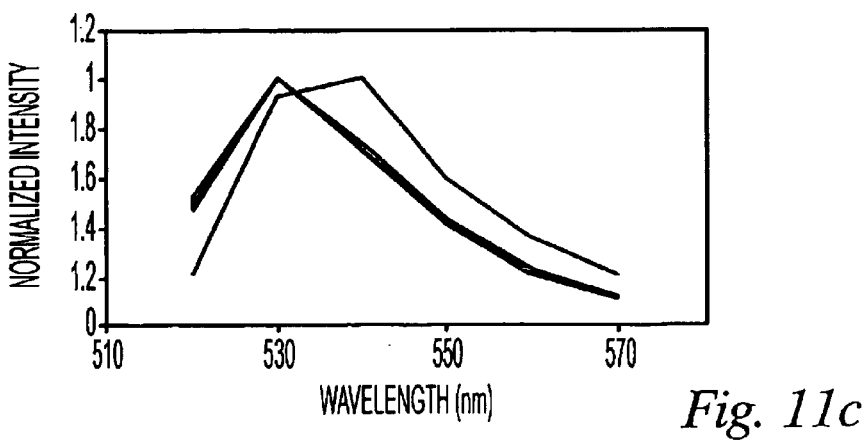

A similar setup has been used for capillary zone electrophoresis. The protein samples are injected into the individual capillary of a 96-capillary array. The capillaries of ID 50 um, OD 150 um, total length 35 cm and effective length of 25 cm are used for the experiment. The separation is taken place at 150 V/cm. The borate buffer at pH 10.5 was the separation medium. The samples are mixtures of proteins injected with a vacuum (hydrodynamical injection). One standard with different emission spectra from the proteins is added to the sample for quantitative analysis. The data of 6 wavelengths are collected to resolve the 2 unknowns as in FIG. 11a. After the computer program picks up the bands and then recognize the spectra pattern as in FIG. 11c, the two traces of data are shown in FIG. 11b after the matrix deconvolution.

Example D—Different Dye Sets Used in the Same Capillary Array

The techniques discussed herein have been used to automatically obtain the calibration coefficients for different dye sets commonly used in DNA sequencing. The methodology includes peak classification, initial peak rejection, coefficient determination, refined peak rejection, and color de-convolution.

Figure 12:
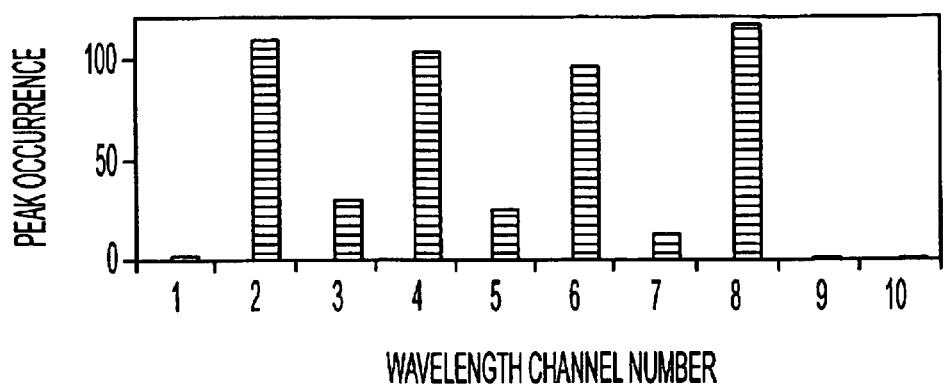
FIG. 12 represents an experimental histogram of peaks from a DNA sequencing example.

(1) Peak classification. To automatically calibrate a single dye set, a tagged DNA sample was introduced into a single capillary and electrophoresced. Approximately 500 bases in a single electropherogram were detected, each base giving rise to a peak within the set of 10 channels. The peaks were then classified according to the channel in which their intensity was a maximum. First, peak positions and intensities were recorded and metrics such as average peak spacing in the time domain and average peak intensity were also calculated. In general, when a peak shows up in one channel, a peak often shows up in the other channels in the time domain at the same time. This is because each member within a dye family causes some overlap among the 10 contiguous channels. At the specific time that a peak shows up, the intensities of the peaks over the ten wavelength channels were compared to determine in which of the 10 channels, a peak exhibited maximum intensity. The channel numbers in which the maximum intensity of a peak was found was recorded for each peak, and this was histogrammed. FIG. 12 shows a histogram of the maximum intensities among the wavelength channels, indicating that peak maxima were most frequently detected in channels 2, 4, 6 and 8. This corresponds to the spectral peak of the four bases among the 10 contiguous channels. Thus, though some peak maxima were found in all 10 channels, these four channels were dominant.

(2) Initial peak rejection. Three kinds of peaks were rejected prior to the calculation of calibration coefficients. First, peaks whose maximum intensities did not fall into any of channels 2, 4, 6, 8 were rejected and eliminated from consideration. Second, peaks which overlapped in the time domain were also rejected. Two peaks were considered to overlap if the spacing between two adjacent peaks in time domain was smaller than 80% of average spacing distance between peaks. Third, low intensity peaks, defined as those peaks having a maximum peak intensity less than 20% of the average peak intensity, were also rejected from further consideration. After initial peak rejection, only about 300 of original 500 peaks remained left as candidates for use in calculating calibration coefficients.

(3) Calculation of the average coefficients and their standard deviation. The maximum intensity of the remaining 300 or so peaks was first normalized to 1.0000, the normalization being done in the wavelength domain. In other words, if the maximum for a peak was in channel 2, indicating a "G" base for a particular set of dyes, the 10 coefficients for the "G" base for this particular peak were calculated as the ratio of the intensity in each of the 10 channels to the intensity found in channel 2 for that peak. Thus, the set of calibration coefficients for base G is derived from those remaining 300 peaks whose maximum intensity was found in channel 2, by normalizing each such peak in the wavelength domain and taking the averages of each of the 10 sets coefficients. Similarly, the set of calibration coefficients for the A, T and C bases were calculated from those remaining 300 peaks whose maximum intensities were found in channels 4, 6 and 8, respectively. The 10 group coefficient averages and the 10 group standard deviations for each of the four groupings (G, A, T and C) is then calculated for further processing.

(4) Additional peak rejection. If the difference between any one of the 10 normalized coefficients for a peak within a particular group (G, A, T or C) and the group average for that coefficient is bigger than a predetermined times (e.g., 1.5 times) the group standard deviation for that coefficient, that peak is rejected and not used in coefficient calculations.

(5) Matrix formation. After the additional peak rejections have been performed, the average coefficients for each group are calculated to establish the calibration matrix.

(6) Color deconvolution. Given the output from the detector, equation 3 is used in conjunction with the appropriate calibration matrix to calculate the four base intensities. This results in color deconvolution of the signals.

Calibration coefficient matrices were calculated for the Spectrumedix Model SCE 9610 Genetic Analysis System for each of the following dye sets: ABI BigDye terminator dye set, ABI Rhodamine terminator dye set, Amersham ET primer dye set, and Baylor Bodipy dye set. The resulting matrices are shown in FIGS. 13a–13d. The data in the first column of each matrix represents the averaged intensity distribution over the 10 channels for a base emitting the shortest wavelength. The second, third and fourth columns represent coefficients of the bases emitting increasingly longer wavelengths during fluorescence, with the fourth column representing the coefficients of a base that emits in the longest wavelength fluorescence.

As is known to those skilled in the art, Bodipy dyes have narrow emission spectrum and small wavelength spacing (20 nm) between adjacent dyes. To accommodate Bodipy dyes, only two adjacent pixels, rather than three, were binned so as to give high spectral resolution. The new matrix, which is based on two-pixel binning for each channel, dramatically enhances results using Bodipy dyes for DNA sequencing.

Because each lane in a multi-lane electrophoretic separation system can have its own calibration matrix, one can use multiple dye sets at the same time, only a single dye set being used to tag the sample in each lane. This allows one to divide a sample into two or moieties, tag each moiety with a different dye set, and compare the results of performing separation of the sample, as tagged with different dye sets. Thus, one can directly compare the performance of different dye sets without changing instrument set-up, such as using a different set of filters. In samples that have been separated using an array of capillaries, different combinations of the dye sets have been used to tagged samples, with each capillary having therein a sample tagged with only one dye set.

Peak Selection and Basecalling Using 3-D Pattern Recognition

In the above discussion, various heuristic and statistical techniques are used to select peaks whose underlying data are used to form calibration matrices, especially in DNA sequencing applications. An alternative approach to select peaks to be used for coefficient calculation is to identify solitary peaks in topographic plots of time-frequency plots.

Figure 14:
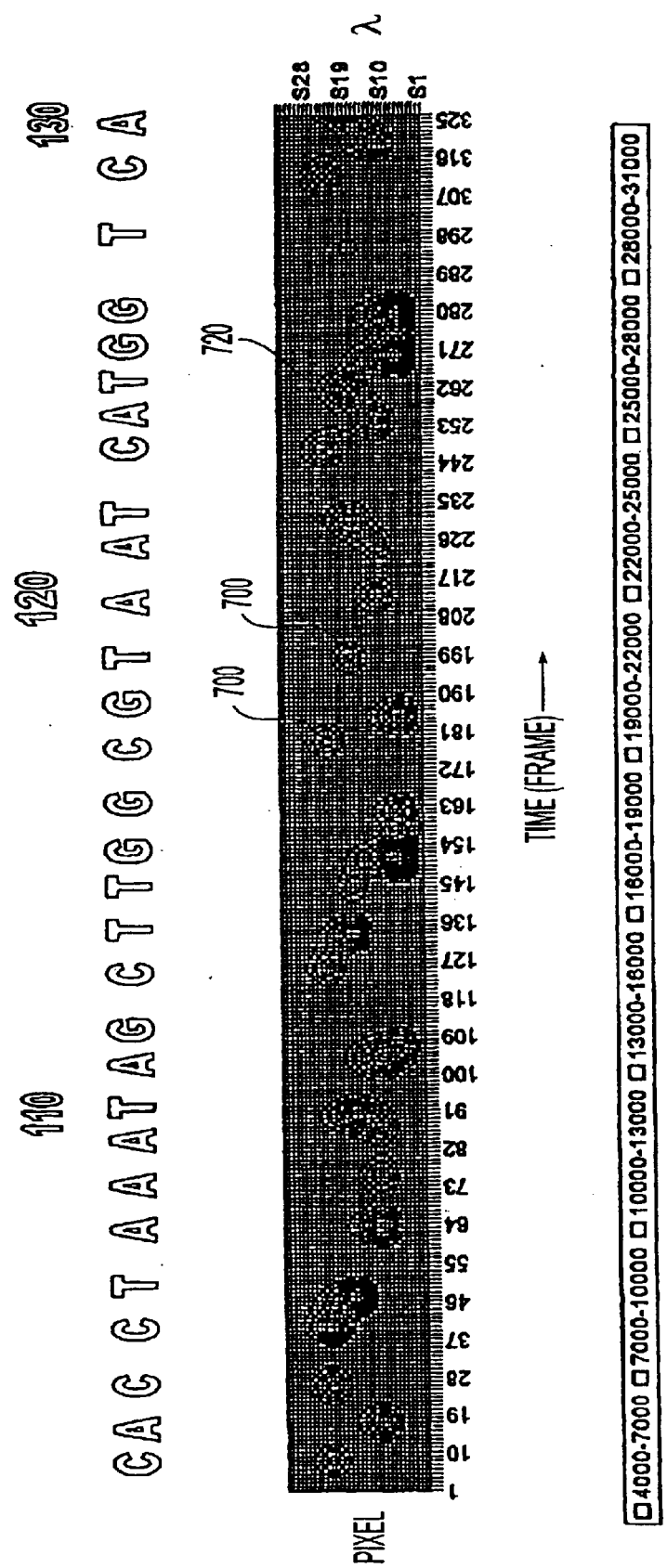
FIGS. 14, 15 and 16 shows contoured time-frequency plots for the beginning middle and terminal portions, respectively, for an electrophoresis run of a DNA sample in a single capillary.
Figure 15:
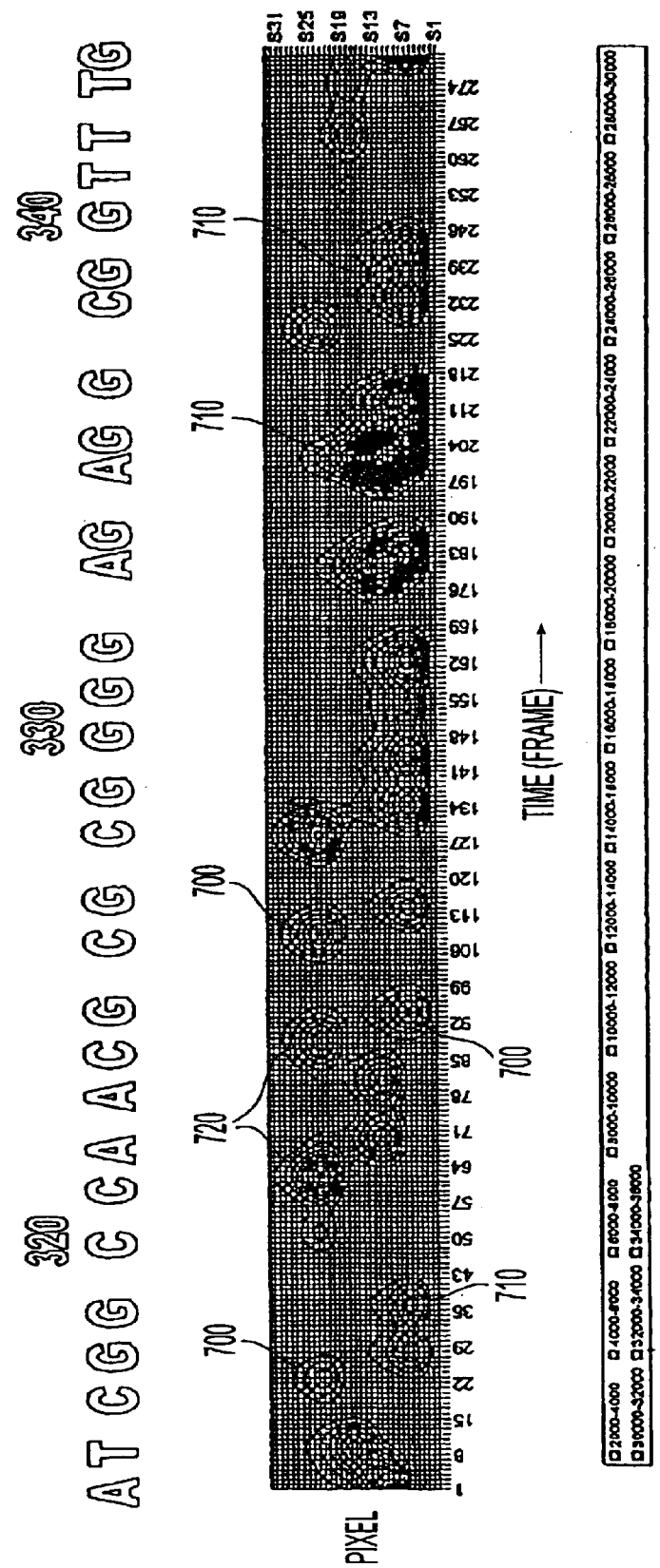
Figure 16:
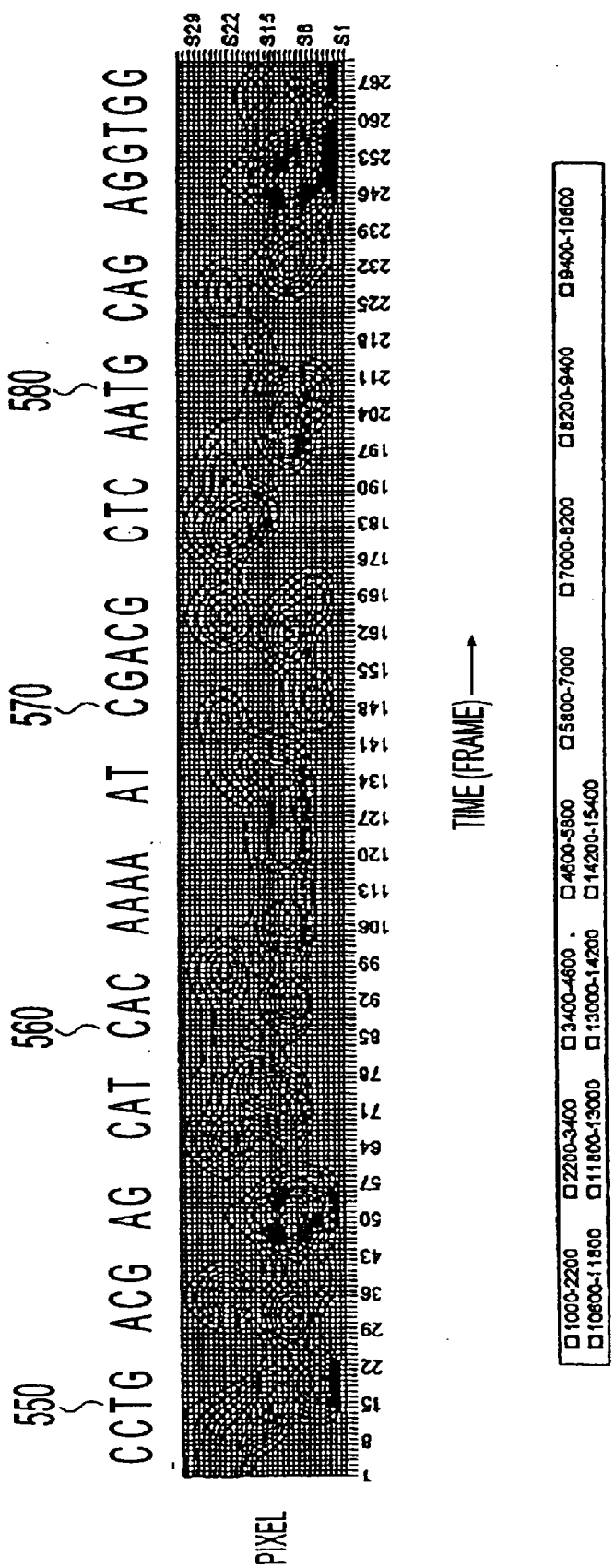

FIGS. 14–16 show time-frequency plots from sequencing a DNA sample, in a capillary, using the Spectrumedix SCE 9610 instrument. In FIGS. 14–16, the x-axis represents a time element, as manifested by the frame number of the detector output. As seen in these figures, a single peak occupies several frames in the time dimension, the exact number depending on the rate of sample migration and the speed at which the fluorescence is sampled by the detector. The y-axis represents the pixel position, which relates to wavelength at 5 nm/division starting at 520 nm, with a total of 35 points, effectively serving as 35 channels, in the y dimension. As also seen in FIGS. 14–16, a single peak occupies more than one frame in the wavelength dimension due to the overlapping spectrum of each dye. The contours associated with each peak, i.e., the flattened "z" axis, corresponds to the intensity of that peak.

FIGS. 14–16 exhibit peaks with different morphologies. Single, solitary peaks 700 which do not overlap with other peaks are circular, or slightly oval in shape. The data corresponding to such isolated peaks can be used to create calibration coefficients. Peaks which have merged together to form conjoined twin peaks 710, or multiple sets of connected peaks 720, preferably are rejected when calculating calibration coefficients. Thus, by first plotting the data in the form of a time-frequency plots, one can first identify solitary peaks and then group together solitary peaks corresponding to the same base (or other tagged species). Given the isolated peaks, their underlying data can be used to normalize each peak, and perform other operations necessary in the calculation of the coefficient matrices.

FIG. 14 shows an early part of the sample separation between base pairs 100–130; FIG. 15 shows a middle part of the sample separation between base pairs 320–440 and FIG. 16 shows a terminal part of the time-frequency plots. It is noted that the morphological features are better separated from one another in the early and middle parts of the sample separation. This is because the corresponding fragments are smaller, and therefore more distinct in the time domain, as they migrate. Accordingly, when using morphology to identify candidate peaks, one may prefer to use time-frequency plots from shorter fragments, i.e., the fragments which migrate earlier on.

The plots of FIGS. 14–16 also suggest an alternative to using Equation 3 to perform color deconvolution of the received channel data, in conjunction with a calibration matrix. This alternative is to directly identify the morphological shapes in a time-frequency plot. Thus, in the case of FIGS. 14–16, one can perform direct basecalling without first having to calculate calibration matrices. Direct basecalling may be more accurate when dealing with overlapped peaks because pairs of adjacent peaks exhibit fairly consistent appearances.

FIG. 17 shows isolated examples of different morphologies. FIG. 17a shows a single peak; FIG. 17b shows double overlapped peaks with the same base in which the twin peaks appear as an elongated oval in the time domain; FIGS. 17c and 17d shows double overlapped peaks with the different bases; and FIGS. 17e, 17f and 17g shows three adjacent overlapped peaks.

Identification of the solitary peaks, and direct basecalling, can be performed either visually by humans, or automatically by using machine-based image processing or pattern recognition techniques, well known to those skilled in the art of computer vision. Thus, in the case of machine-based processing, morphological filters can be used as templates to identify the features seen in FIG. 17.

While the above invention has been described with reference to certain preferred embodiments, it should be kept in mind that the scope of the present invention is not limited to these. One skilled in the art may find variations of these preferred embodiments which, nevertheless, fall within the spirit of the present invention, whose scope is defined by the claims set forth below.

What is claimed is:

1. A method of calibrating a detection system in an electrophoresis apparatus comprising at least one separation lane, the detection system configured to sense a spectrum of light intensities over a number in wavelength channels from said at least one separation lane, the method comprising:

detecting at least one spectrum of light intensities for each of a plurality of samples;

clustering the detected spectra of light intensities into a number n categories by using at least one specified clustering criterion, the step of clustering comprising:

normalizing light intensities of each of the detected spectra by a respective normalization value to prepare spectra comprising normalized light intensities;

comparing corresponding normalized light intensities of different spectra; and clustering detected spectra that do not have compared corresponding normalized light intensities differing by more than the specified clustering criterion; and creating a calibration matrix from the clusters.

2. The method according to claim 1, wherein detected spectra of at least some samples are discarded prior to the clustering step.

3. The method according to claim 1, wherein a calibration matrix is determined for each of a corresponding plurality of separation lanes.

4. The method according to claim 3, wherein a total of at least 96 calibration matrices are generated, one for each of a corresponding separation lane.

5. A method for automatically calibrating an electrophoresis separation apparatus having a plurality of separation lanes, the method comprising the steps of:

for each separation lane, detecting a plurality of sets of light intensities from a migrating sample, the light intensities in each set being collected in a total of R channels, where $R \geq 2$;

for each separation lane, identifying isolated peaks in at least some of the plurality of sets of light intensities;

estimating a number of dyes M present in the migrating sample based on the isolated peaks, where $M \geq 2$;

for each separation lane, calculating coefficients based on the distribution of light intensities in channels corresponding to the isolated peaks, wherein the coefficients map detected light intensities from the R channels onto values reflective of the relative likelihood of each of the dyes being present;

wherein estimating a number of dyes comprises:

normalizing light intensities of each of the respective sets of light intensities with respect to a respective normalization value;

comparing normalized light intensities of different sets of light intensities;

clustering detected sets of light intensities that do not have compared corresponding normalized light intensities differing by more than a specified clustering criterion; and preparing a calibration matrix using the clustered sets of light intensities.

6. A method according to claim 5, wherein the coefficients are arranged in the form of an R×M matrix.

7. A method for automatically calibrating a separation apparatus, said method comprising the steps of:

sampling light emitted from species having a chromophore, the sampling being performed over a first number m of wavelength channels and a second number n of time intervals to thereby form a time-wavelength distribution wherein a total of k discrete species are represented by morphological formations in the time-wavelength distribution;

isolating a total of l peaks from said formations, each peak corresponding to a discrete species;

clustering the l peaks into a number j classes based on at least one similarity criterion, wherein clustering the l peaks comprises:

normalizing wavelength values of the time-wavelength distribution; and identifying peaks that do not have corresponding normalized wavelength values differing by more than the at least one similarity criterion;

forming a total of j calibration vectors, each calibration vector representing one of said classes; and forming a calibration matrix A comprising the j calibration vectors.

8. The method of claim 7, wherein isolating l peaks from the formations comprises:

preprocessing the sample data in the time domain;

isolating a total of p peaks in the time domain; and isolating a total l peaks from p peaks according to the width and spacing of said peaks in the time domain.

9. The method of claim 7, wherein the step of isolating peaks comprises employing morphological filters to identify peaks in the time-wavelength distribution.

10. The method of claim 7, wherein the step of isolating peaks comprises visually inspecting the time-wavelength distribution and selecting those peaks which are unconnected to other peaks.

11. A method for calibrating an electrophoresis system, comprising:

electrophoretically separating a sample along a separation lane;

obtaining, at a number t different times, a spectrum indicative of the presence of sample components separated along the separation lane, each spectrum comprising a number x intensity values, the x intensity values of each spectrum being indicative of an intensity at a different wavelength;

normalizing a plurality of the x intensity values of each of a plurality of the t spectra to a respective normalization value;

clustering spectra having normalized intensity values by steps comprising:

(a) comparing normalized intensity values of a first one of the spectra with corresponding normalized intensity values of another spectrum;

(b) assigning the other spectrum to a first cluster including the first spectrum if a maximum difference between the compared normalized fluorescence intensity values of the first spectrum and the other spectrum is less than a specified value;

(c) repeating the comparing and assigning steps until normalized fluorescence intensity values of all of the other spectra have been compared with corresponding normalized fluorescence intensity values of the first one of the spectra;

(d) comparing normalized fluorescence intensity values of a second spectrum, the second spectrum not assigned to a cluster, with corresponding normalized fluorescence intensity values of another spectrum not assigned to a cluster;

(e) assigning the other spectrum of step (d) to a new cluster including the second spectrum if a maximum difference between the compared normalized fluorescence intensity values of the second spectrum and the other spectrum of step (d) is less than a specified value;

(f) repeating the (d) comparing and (e) assigning steps until all of the other spectra not yet assigned to a cluster have been compared with the second spectrum; and (g) repeating the (d) comparing, (e) assigning, and (f) repeating steps until all of the spectra have been assigned to a respective cluster.

12. A method for processing separations data, comprising:

electrophoretically separating a sample along a separation lane in the presence of a number n fluorescent dyes, the fluorescence of each of the n dyes being indicative of the presence of a different component of the sample, each dye having a different fluorescence spectrum;

obtaining, at a number t different times, a fluorescence spectrum indicative of the presence of one or more components of the sample separated along the separation lane, each spectrum comprising a number x intensity values, the x intensity values of each spectrum being indicative of an intensity at a respective, different wavelength;

normalizing a plurality of the x intensity values of a plurality of the t spectra to a respective normalization value;

selecting a number n subsets of the spectra with normalized x intensity values, the members of each subset determined by comparing the normalized intensity values of respective spectra with corresponding normalized intensity values of at least one of the other spectra and clustering in a subset those spectra that do not have compared corresponding normalized intensity values differing by more than a specified value.

13. The method of claim 12, wherein the spectra of each one of the n subsets are indicative of the presence of one of the n dyes.

14. The method of claim 13, wherein the number n subsets comprise fewer than t members and the method further comprises using the members of the n subsets to determine the presence of the n dyes in the spectra not clustered in one of the n subsets.

15. The method of claim 14, wherein using the members of the n subsets comprises creating a calibration matrix from the n subsets.

16. The method according to claim 15, wherein a calibration matrix is determined for each of a corresponding plurality of separation lanes.

* * * * *